United States Patent [19]

Bar-Tana et al.

[11] Patent Number: 4,908,385
[45] Date of Patent: Mar. 13, 1990

[54] α-HALOGENATED DICARBOXYLIC ACIDS, PHARMACEUTICAL COMPOSITIONS AND METHOD OF USE

[75] Inventors: Jacob Bar-Tana; Yoelit Migron; Jochanan Blum, all of Jerusalem, Israel; Bruno Dreckmann, Mannheim; Johannes Pill, Leimen, both of Fed. Rep. of Germany

[73] Assignee: Epis S.A., Zug, Switzerland

[21] Appl. No.: 106,557

[22] Filed: Oct. 6, 1987

[30] Foreign Application Priority Data

Oct. 8, 1986 [DE] Fed. Rep. of Germany ....... 3634356

[51] Int. Cl.⁴ .................. A61K 31/19; A61K 31/225; A61K 31/16; C07C 55/32
[52] U.S. Cl. ..................................... 514/574; 514/547; 514/616; 560/192; 562/596; 564/160
[58] Field of Search ........................ 560/192; 562/596; 564/160; 514/547, 574, 616

[56] References Cited

U.S. PATENT DOCUMENTS

| | | | |
|---|---|---|---|
| 2,971,915 | 2/1961 | Borsoff et al. | 562/590 X |
| 3,678,102 | 7/1972 | Isard et al. | 560/190 X |
| 3,776,951 | 12/1973 | Failey et al. | 560/590 |
| 4,634,795 | 1/1987 | Bar-Tana | 560/192 X |
| 4,689,344 | 8/1987 | Bar-Tana | 514/527 |

OTHER PUBLICATIONS

Schisla, et al., *J. Org. Chem.*, vol. 35, No. 10, pp. 3224–3230, 1970.
Simmonds, *J.Biochem.* 58, 520-3, (1954).
Anderson et al., *J. Org. Chem.* 31, 3890-7, (1966).
Khavasch, *J. Org. Chem.* 23, 1322-6, (1958).
Treibs et al., *Chem. Ber.*, 93, 2198-2208, (1960).
Chem. Abstr., 76, 55097m: Cherepenko, (1972).

*Primary Examiner*—Werren B. Lone
*Assistant Examiner*—Vera C. Clarke
*Attorney, Agent, or Firm*—Felfe & Lynch

[57] ABSTRACT

The present invention provides pharmaceutical compositions containing at least one α-halogenated dicarboxylic acid of the general formula:

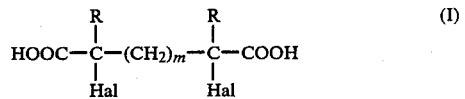

wherein Hal is a chlorine, bromine or fluorine atom, R is a hydrogen atom or Hal and m is a number of from 4 to 16, and/or at least one pharmacologically acceptable salt, ester or amide thereof.

The present invention also provides new compounds of general formula (I) but in which m is a number of from 8 to 16 and processes for the preparation thereof.

11 Claims, No Drawings

α-HALOGENATED DICARBOXYLIC ACIDS, PHARMACEUTICAL COMPOSITIONS AND METHOD OF USE

The present invention is concerned with pharmaceutical compositions, with new pharmaceutically-active compounds and with the preparation thereof.

Thus, according to the present invention, there are provided pharmaceutical compositions containing at least one α-halogenated dicarboxylic acid of the general formula:

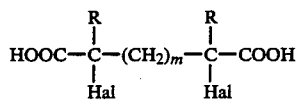    (I)

wherein Hal is a fluorine, chlorine or bromine atom, R is a hydrogen atom or Hal and m is a number of from 4 to 16, and/or at least one in vivo hydrolysable, pharmacologically acceptable salt, ester or amide thereof.

These pharmaceutical compositions are useful for the treatment of adipositas, hyperlipidaemia and diabetes.

Some α,α'-dihalodicarboxylic acids and α,α,α',α'-tetrahalodicarboxylic acids, as well as derivatives thereof, which come within the ambit of general formula (I) have long since been described in the literature, especially those derivatives in which m is less than 8, but no pharmacological effectiveness has been described for these compounds.

We have now, surprisingly, found that compounds of general formula (I), as well as the in vivo hydrolysable derivatives thereof, display an outstanding lipid-sinking and antidiabetic action. They are able not only to lower the triglyceride and also the serum cholesterol level but are also agents for the prophylaxis and treatment of arteriosclerotic diseases. In the case of overweight patients, they bring about a reduction of body weight and, in the case of type II diabetes, improve the glucose metabolism.

The present invention also provides new, long-chained α-halogenated dicarboxylic acids of the general formula:

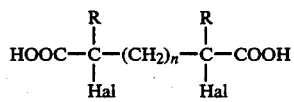    (I')

wherein Hal is a fluorine, chlorine or bromine atom, R is a hydrogen atom or Hal and n is a number of from 8 to 16, as well as the in vivo hydrolysable carboxylic acid derivatives thereof, with the exception of the compounds 2,11-dichlorododecane-1,12-dioic acid, diethyl 2,11-dibromododecane-1,12-dioate, dimethyl 2,2,15,15-tetrabromohexadecane-1,16-dioate and N,N'-dimethyl-2,2,15,15-tetrabromohexadecanediamide.

The compounds mentioned in the disclaimer are already known but, in all cases, there are no statements regarding a pharmacological effectiveness: 2,11-dichlorododecane-1,12-dioic was described in J. Org. Chem., 23, 1322-1326/1958; diethyl 2,11-dibromododecane-1,12-dioate in J. Org. Chem., 31, 3890-3897/1966; and dimethyl 2,2,15,15-tetrabromohexadecane-1,16-dioate and N,N'-dimethyl-2,2,15,15-tetrabromohexadecanediamide in Chem. Ber., 93, 2198-2208/1960.

In vivo hydrolysable derivatives of compounds of general formulae (I) and (I') are, for example, salts with pharmacologically acceptable alkali metal, alkaline earth metal and ammonium bases; esters and especially $C_1$-$C_6$-alkyl esters, for example methyl, ethyl and isopropyl esters; amides, the nitrogen atom of which can be mono- or disubstituted with $C_1$-$C_6$-alkyl radicals, for example N-methylamides and N,N-dimethylamides.

The compounds of general formula (I) can be prepared in known manner, for example:

(a) when R is a hydrogen atom, a dicarboxylic acid of the general formula:

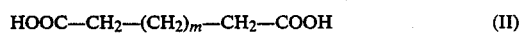    (II)

in which m is a number from 4 to 16, or a derivative thereof, is reacted with an appropriate halogenation agent to give the corresponding α,α'-dihalocarboxylic acid; or (b) when R is a halogen atom, (b1) an α;ω-dicarboxylic acid of general formula (I), in which R is a hydrogen atom and m is a number from 4 to 16, is reacted with a base and subsequently with a halogenation agent to give a compound of general formula (I), in which R is a halogen atom; or (b2) a compound of the general formula:

    (III)

in which Hal has the above-given meaning, or a derivative thereof is reacted under basic conditions with a compound of the general formula:

    (IV)

in which m has the above-given meaning and Y is a residue which can easily be split off; whereafter, if desired, a compound obtained of general formula (I) is converted into another compound of general formula (I) and, if desired, an ester, amide or salt obtained is converted into the free acid or a free acid obtained is converted into an ester, amide or salt.

The term "acid" used in the following in the case of compounds of general formulae (I), (I'), (II) and (III) is also to be understood to include the corresponding acid halides, esters and amides.

As halogenation agents, there can be used the usual compounds described in the literature and especially those which contain a positive polarised halogen atom, for example N-chlorosuccinimide, sodium N-chloro-4-toluenesulphonic acid amide, N-bromosuccinimide, N-bromoacetamide, dibromodimethylhydantoin, xenon fluorides, hydrogen fluoride/pyridine mixtures, fluoroxytrifluoromethane and the like, optionally in the presence of an appropriate catalyst, for example iodine or iron.

The reaction can be carried out in the presence of an inert solvent or solvent mixture. Appropriate solvents include, for example, hydrocarbons, such as heptane, methylcyclohexane and benzene, chlorinated and fluorinated hydrocarbons, such as methylene chloride, chloroform and carbon tetrachloride. If possible, the reaction is preferably carried out without the use of a solvent. If the corresponding acid halides of the compounds of general formula (I) are used, the halogenation agent used for converting the free acids into the acid halides can also be employed in excess as solvent.

According to process (a), the α,α'-dihalo acids of general formula (I) can be obtained by reaction with halogenation agents, for example N-bromosuccinimide, N-chlorosuccinimide and the like. The reaction takes place at a temperature of from 0° C. and ambient temperature and possibly also at a temperature up to the boiling point of the solvent.

According to process (b), there are prepared α,α,α',α'-tetrahalodicarboxylic acids of general formula (I). In process (b), α,α'-dihalodicarboxylic acids are used as starting materials which, under basic conditions, are converted into the corresponding carbanion derivatives. These are reacted with appropriate halogenation agents to give the tetrahalo compounds. This process is especially useful for the preparation of mixed tetrahalodicarboxylic acids, for example α,α'-dibromo-α,α'-difluorodicarboxylic acids, α,α'-dibromo-α,α'-dichlorodicarboxylic acids and α,α'-dichloro-α,α'-difluorodicarboxylic acids. As base, there can be used, for example, lithium diisopropylamide or n-butyl lithium. The solvent used can be an inert organic solvent. The reaction is carried out at a temperature of from 0° to −80° C. in the presence of an appropriate halogen transfer agent, for example carbon tetrachloride, carbon tetrabromide or the like. According to process (b2), a dihaloacetic acid or a derivative thereof is converted with a strong base, for example lithium diisopropylamide, butyl lithium or the like, in an inert organic solvent into the corresponding carbanion derivative. Dichloroacetic acid chloride is preferably used. The subsequent reaction of a compound of general formula (III) with a compound of general formula (IV) preferably takes place in a mole ratio of 2:1. As residues Y in compounds of general formula (III) which can easily be split off, there can be used, for example, bromo, chloro or sulphonyloxy compounds, for example trifluoromethylsulphonyloxy, methylsulphonyloxy or 4-chlorophenylsulphonyloxy radicals. The reaction takes place in an inert organic solvent, preferably in tetrahydrofuran and hexamethylphosphoric acid triamide (HMPT) at a temperature of from −80° C. to ambient temperature.

The subsequent conversion of compounds of general formula (I) or (I') refers, inter alia, to the preparation of fluorinated compounds which can be prepared from the corresponding bromo or chloro compounds with the help of appropriate fluorination agents for example tetrabutylammonium fluoride or nitrosyl fluoride.

The conversion of esters obtained into the corresponding free acids takes place under strongly acidic conditions. In the case of dicarboxylic acids of general formula (I) or (I'), in which R is a hydrogen atom, the conversion of the esters into the free acids takes place in the usual way by gentle alkaline saponification. This method is unsuitable for esters in which R is a halogen atom. In this case, it is preferable to start from the isopropyl esters which can be converted into the free acids by means of concentrated sulphuric acid plus oleum. The conversion of acid halides into free acids takes place by hydrolysis. The salts are obtained in the usual way, for example by neutralising compounds of general formula (I) with appropriate lyes.

For the preparation and subsequent conversion of compounds of general formula (I'), there apply, in an analogous way, the processes described above for compounds of general formula (I).

For the preparation of pharmaceutical compositions, the compounds of general formula (I) or (I') are mixed in the usual way with appropriate pharmaceutical carrier substances, aroma, flavouring and colouring materials and formed, for example, into tablets or dragees or, with the addition of appropriate adjuvants, for example water or an oil, such as olive oil, are suspended or dissolved.

The compounds of general formula (I) or (I') can be administered orally or parenterally in liquid or solid form. As injection medium, water is preferably used which contains the stabilising agents, solubilising agents and/or buffers usual in the case of injection solutions. Such additives include, for example, tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbit anhydrides. Solid carrier materials include, for example, starch, lactose, mannitol, methyl cellulose, talc, highly dispersed silicic acid, high molecular weight polymers (such as polyethylene glycol). Compositions suitable for oral administration can, if desired, contain flavouring and sweetening agents.

The dosage administered depends upon the age, state of health and weight of the recipient, the extent of the disease, the nature of further treatments possibly carried out simultaneously, the frequency of the treatment and the nature of the desired action. The daily dose of the active compound is usually from 0.1 to 50 mg. per kg. of body weight. Normally, 0.5 to 40 mg. and preferably 1.0 to 20 mg. per kg. per day, in one or more administrations per day, are effective in order to achieve the desired results.

Apart from the compounds mentioned in the Examples, the following compounds, as well as the methyl, ethyl and isopropyl esters and amides, are also preferredaccording to the present invention:

(1) 2,7-dichlorooctane-1,8-dioic acid
(2) 2,7-difluorooctane-1,8-dioic acid
(3) 2,7-dibromooctane-1,8-dioic acid
(4) 2,2,7,7-tetrachlorooctane-1,8-dioic acid
(5) 2,2,7,7-tetrabromooctane-1,8-dioic acid
(6) 2,8-dichlorononane-1,9-dioic acid
(7) 2,2,8,8-tetrabromononane-1,9-dioic acid
(8) 2,11-dichlorododecane-1,12-dioic acid
(9) 2,2,11,11-tetrabromodedecane-1,12-dioic acid
(10) 2,12-difluorotridecane-1,13-dioic acid
(11) 2,13-dichlorotetradecane-1,14-dioic acid
(12) 2,2,13,13-tetrachlorotetradecane-1,14-dioic acid; m.p. 94°–97° C.
(13) 2,15-difluorohexadecane-1,16-dioic acid
(14) 2,15-dibromohexadecane-1,16-dioic acid
(15) 2,15-dichlorohexadecane-1,16-dioic acid
(16) 2,15-dichloro-2,15-difluorohexadecane-1,16-dioic acid
(17) 2,15-dibromo-2,15-difluorohexadecane-1,16-dioic acid
(18) 2,15-dibromo-2,15-dichlorohexadecane-1,16-dioic acid
(19) 2,2,15,15-tetrabromohexadecane-1,16-dioic acid
(20) 2,17-dichlorooctadecane-1,18-dioic acid
(21) 2,17-dibromooctadecane-1,18-dioic acid
(22) 2,2,17,17-tetrachlorooctadecane-1,18-dioic acid
(23) 2,2,17,17-tetrabromooctadecane-1,18-dioic acid
(24) 2,17-difluorooctadecane-1,8-dioic acid
(25) 2,19-dichloroeicosane-1,20-dioic acid
(26) 2,19-difluoroeicosane-1,20-dioic acid

(27) 2,2,19,19-tetrachloroeicosane-1,20-dioic acid
(28) 2,2,19,19-tetrabromoeicosane-1,20-dioic acid.

It will be understood that the specification and examples are illustrative but not limitative of the present invention and that other embodiments within the spirit and scope of the invention will suggest themselves to those skilled in the art.

The following Examples are given for the purpose of illustrating the present invention:

EXAMPLE 1

2,2,15,15-Tetrachlorohexadecane-1,16-dioic acid (a) Isopropyl dichloroacetate 9 g. (60 mMole) Dichloroacetyl chloride are added dropwise to 20 g. isopropanol cooled to 3° C. in an ice/water bath. The reaction solution is further stirred for 30 minutes at ambient temperature, whereafter excess alcohol is removed in a vacuum at ambient temperature. The residue is subsequently mixed with a mixture of ice water and dichloromethane. After separation of the phases, the organic phase is successively washed with water, aqueous sodium hydrogen carbonate solution and again with water and dried over anhydrous sodium sulphate. After removal of the solvent, there are obtained 7.5 g. (73% of theory) isopropyl dichloroacetate which, after distillation (67°–68° C., 24 hPa) is obtained as a colourless liquid.

(b) Diisopropyl 2,2,15,15-tetrachlorohexadecane-1,16-dioate

A solution of 2.02 g. (20 mMole) dry diisopropylamine in 20 ml. tetrahydrofuran is placed into a three-necked flask under an atmosphere of dry nitrogen. The solution is cooled in an icebath to 3° C. and a solution of 14 ml. of a 1.42 molar solution of n-butyl lithium in hexane (20 mMole) injected therein, while stirring. The solution is stirred for 30 minutes at 3° C., then cooled to −78° C. and 20 ml. hexamethylphosphoric acid triamide (HMPT) added thereto. The reaction mixture becomes yellow and viscous. After a further 30 minutes at −78° C., a solution of 3.42 g. (20 mMole) isopropyl dichloroacetate in 20 ml. dry tetrahydrofuran is added thereto, while stirring. After 20 minutes at −78° C., a solution of 3.28 g. (10 mMole) 1,12-dibromododecane in 20 ml. dry tetrahydrofuran is added dropwise thereto at −78° C. and the solution is further stirred for 35 minutes. Within the course of 2 hours, the temperature is slowly increased to −20° C., the solution is further stirred for 30 minutes at −20° C. and then poured on to ice/concentrated sulphuric acid. After extraction with petroleum ether (b.p. 40°–60° C.) and usual working up, there is obtained an oily residue. After chromatography on silica gel and elution with a linear gradient of dichloromethane and petroleum ether (b.p. 40°–60° C.), there are obtained 3.5 g. (yield 68% of theory) diisopropyl 2,2,15,15-tetrachlorohexadecane-1,16-dioate as a colourless solid material.

(c) 3 g. of a mixture of 96–98% sulphuric acid and oleum (1:1 w/w) cooled to 3° C. are added dropwise to the dry diisopropyl 2,2,15,15-tetrachlorohexadecane-1,16-dioate. The mixture is stirred for 10 minutes at 3° C., a colour change to orange thereby taking place. A further 2 g. of the acid mixture are added dropwise until the ester has completely dissolved and then stirred for 15 minutes at 3° C. The solution is cooled to −78° C. and a mixture of ice/dichloromethane added thereto. The frozen mixture is dissolved by slowly warming to ambient temperature while stirring with a porcelain spatula, the solution thereby becoming colourless. After separation of the phases, the aqueous phase is extracted with dichloromethane and the combined organic extracts are dried over anhydrous sodium sulphate. After removal of the solvent, there are obtained 150 mg. (yield 90% of theory) of a colourless solid; m.p. 113.5°–114.5° C., after recrystallisation from cyclohexane.

EXAMPLE 2

2,15-Dichlorohexadecane-1,16-dioic acid 572 mg. (2 mMole) Hexadecane-1,16-dioic acid are dissolved in 20 ml. thionyl chloride and heated under reflux for 30 minutes. The formation of the acyl chloride is monitored IR-spectroscopically (increase of the peak at 1790 cm$^{-1}$ (COCl) and decrease of the peak at 1695 cm$^{-1}$ (COOH)). The reaction mixture is cooled to ambient temperature, a solution of 1.068 g. (8 mMole) N-chlorosuccinimide in 20 ml. thionyl chloride is added thereto and the mixture heated under reflux for a further 4.2 hours. Excess thionyl chloride is removed in a vacuum at ambient temperature, some carbon tetrachloride is added thereto and the solution is evaporated to dryness. The residue is mixed with carbon tetrachloride and the solid succinimide is filtered off and washed with carbon tetrachloride. The combined filtrates are cooled to 0°–5° C. and mixed with ice. The ice-water bath is removed, some tetrahydrofuran is added thereto and the solution is vigorously stirred overnight at ambient temperature. After separating off the organic phase, it is evaporated. The oil obtained crystallises out after some time (700 mg., quantitative yield). Recrystallisation from cyclohexane gives 545 mg. of the desired product; m.p. 71°–72° C.

In analogous manner it was obtained: (a) Diisopropyl-2,15-dichlorohexadecane-1,16-dioate; colourless oil.

EXAMPLE 3

2,15-Dibromo-2,15-dichlorohexadecane-1,16-dioic acid

Bromination of diisopropyl 2,15-dichlorohexadecane-1,16-dioate with CBr$_4$ gave diisopropyl 2,15-dibromo-2,15-dichlorohexadecane-1,16-dioate (colourless oil). The saponification of the ester with sulphuric acid/Oleum gave the title compound; m.p. 59°–61° C.

EXPERIMENTAL REPORT

Representative for the new compounds, for the compounds

A=2,15-dichlorohexadecane-1,16-dioic acid and
B=2,2,13,13-tetrachlorotetradecane-1,14-dioic acid,
the lipid-sinking action was determined.

For this purpose the substance to be tested was administered, in each case, to 10 male Sprague-Dawley rats for 14 days at a dosage of 25 mg./kg./d. and 200 mg./kg./d. in methyl cellulose suspension. At the end of the experiment, 3 hours before the last probing, the cholesterol and triglyceride values in the serum were determined.

In the following table are given the determined values:

| compound mg./kg./d. | cholesterol values mg./dl. | | triglyceride values mg./dl. | |
| --- | --- | --- | --- | --- |
| | 0. day | 14. day | 0. day | 14. day |
| control | 93 ± 5,1 | 98 ± 5,8 | 129 ± 11 | 108 ± 11,7 |

| compound mg./kg./d. | | cholesterol values mg./dl. | | triglyceride values mg./dl. | |
|---|---|---|---|---|---|
| | | 0. day | 14. day | 0. day | 14. day |
| A | 25 | 90 ± 2,4 | 82 ± 3,5 | 131 ± 11 | 58 ± 5,8 |
| | 200 | 94 ± 6,6 | 53 ± 3,2 | 96 ± 16 | 34 ± 3,0 |
| B | 25 | 102 ± 2,6 | 45 ± 2,9 | 103 ± 12 | 50 ± 4,6 |
| | 200 | 91 ± 5,0 | 32 ± 0,8 | 110 ± 14 | 30 ± 2,2 |

The tested compounds show in comparison to the control and to values before application of the substance a significant cholesterol and lipid sinking effect in the serum of rats.

We claim:

1. A pharmaceutical composition comprising (1) an effective amount of at least one alpha-halogenated dicarboxylic acid compound of the formula:

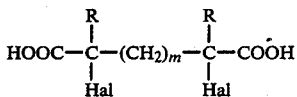

wherein
Hal is chlorine, bromine or fluorine
R is hydrogen or Hal, and
m is a number from 4 to 16,
or at least one pharmaceutically acceptable salt, ester or amide of said compound, and (2) a pharmaceutical carrier.

2. A method for the treatment of adipositas, hyperlipidaemia or diabetes comprising administering a pharmaceutically effective amount of at least one of the compounds of the formula

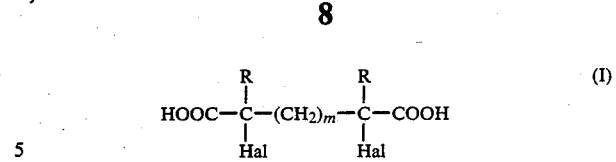

wherein
Hal is chlorine, bromine or fluorine,
R is hydrogen or Hal, and
m is a number from 4 to 16,
or at least one pharmaceutically acceptable salt, ester or amide of said compound to mammals in need of said treatment.

3. A method according to claim 2 wherein the compound used is a $C_1$–$C_6$ alkyl ester.

4. The method of claim 3 wherein the alkyl ester is methyl, ethyl or isopropyl.

5. A method according to claim 2 wherein the compound used is a mono- or disubstituted $C_1$–$C_6$ alkylamide.

6. The method of claim 5 wherein the amide is N-methylamide or N,N-dimethylamide.

7. A method for the treatment of adipositas, hyperlipidaemia or diabetes comprising administering a pharmaceutically effective amount of the compound designated 2,2,13,13-tetrachlortetradecane-1,14-dioic acid to mammals in need of said treatment.

8. The method of claim 2 or 7 wherein the daily dose of the active compound is 0.1 to 50 mg/kg body weight.

9. The method of claim 2 or 7 wherein the daily dose of the active compound is 0.1 to 50 mg/kg body weight.

10. An alpha-halogenated dicarboxylic acid compound designated 2,2,13,13-tetrachlortetradecane-1,14-dioic acid.

11. An alpha-halogenated dicarboxylic acid compound designated 2,15-dichlorohexadecane-1,16-dioic acid.

* * * * *